ent Number: 4,963,586

United States Patent [19]
Katayama et al.

[11] Patent Number: 4,963,586
[45] Date of Patent: Oct. 16, 1990

[54] MICROBICIDAL/MICROBISTATIC COMPOSITION

[75] Inventors: Sakae Katayama, Osaka; Yosuke Ito, Ohtsu; Hidenori Hirashima, Osaka, all of Japan

[73] Assignee: Katayama Chemical, Inc., Osaka, Japan

[21] Appl. No.: 338,609

[22] Filed: Apr. 14, 1989

[30] Foreign Application Priority Data

Apr. 18, 1988 [JP] Japan ................................. 63-96523

[51] Int. Cl.$^5$ ...................... A61K 37/02; A61K 37/06
[52] U.S. Cl. .................................................. 514/547
[58] Field of Search ............................. 514/547, 528; 106/14.13, 14.27, 14.35, 18.32

[56] References Cited

U.S. PATENT DOCUMENTS

| | | | |
|---|---|---|---|
| 3,839,583 | 10/1974 | Shema et al. | 514/528 |
| 3,865,724 | 2/1975 | Shema et al. | 514/528 |
| 4,732,913 | 3/1988 | Donofrio et al. | 514/528 |

FOREIGN PATENT DOCUMENTS

| | | | |
|---|---|---|---|
| 36055 | 11/1981 | European Pat. Off. | 514/547 |
| 141501 | 8/1984 | Japan | 514/547 |

*Primary Examiner*—Douglas W. Robinson
*Assistant Examiner*—Alvin Heindel
*Attorney, Agent, or Firm*—Bryan, Cave, McPheeters & McRoberts

[57] ABSTRACT

A microbicidal/microbistatic synergistic composition for industrial use comprising a specific nitrobromopropane derivative and 2,2-dibromo-3-nitrilopropionamide and an industrial method of killing or inhibiting the growth of microorganisms using the same compounds, which are useful for microbicidal/microbistatic treatment in various industrial media.

11 Claims, 4 Drawing Sheets

MICROBICIDAL/MICROBISTATIC COMPOSITION

BACKGROUND OF THE INVENTION

1. Field of the Invention

The present invention relates to a microbicidal/microbistatic composition for industrial use and method of use. More particularly, it relates to a microbicidal/microbistatic composition for industrial use and a method of killing or inhibiting the growth of microorganisms, which can be used for microbicidal/microbistatic treatment of papermaking process water in paper and pulp industry, cooling water or washing water for various industries, heavy oil sludges, cutting oils, textile oils, paints, antifouling coatings, paper coating liquids, latices, sizings or the like.

2. Description of the Prior Art

Slimes are generated in process water of the paper and pulp industry and cooling water of various industries, due to the growth of bacteria and/or fungi and results in such problems as lowering the quality of products and the efficiency of production. Further, in many industrial products, for example heavy oil sludges, cutting oils, textile oils, paints, various latices and sizings, putrefaction and contamination occur due to the growth of bacteria and fungi which reduces their value.

Thus, many microbicidal agents have been used in order to prevent the problems produced by such microorganisms. Formerly, organomercury compounds, chlorinated phenol compounds and the like were used for this purpose. But these compounds generally show strong toxicity to the human body, fish and shellfish, and cause environmental contamination. Therefore, their use has come to be regulated. Recently, relatively low toxicity compounds such as described below have been used generally as microbicidal compounds for industrial use, namely, organonitrogen-sulfur compounds such as methylene bisthiocyanate, 1,2-benzoisothiazoline-3-one and 5-chloro-2-methyl-4-isothiazoline-3-one; organobromine compounds such as 2,2-dibromo-2-nitroethanol, 2,2-dibromo-3-nitrilopropionamide, 1,2-bis(bromoacetoxy)ethane, 1,4-bis(bromoacetoxy)-2-butene and bistribromomethyl sulfone and the like; and organosulfur compounds such as 4,5-dichloro-1,2-dithiol-3-one.

Such known compounds show different microbicidal spectra and effects and are used corresponding to their working objects. For example, 4,5-dichloro-1,2-dithiol-3-one, 2,2-dibromo-2-nitroethanol, 2,2-dibromo-3-nitrilopropionamide, bistribromomethylsulfone and the like exhibit such activity action that their addition even in small amounts remarkably decreases the number of viable bacteria, (which is referred to as "microbicidal action" hereinafter), but they do not inhibit the growth of viable bacteria for a long period of time, (which is referred to as "antimicrobial (microbistatic) action" hereinafter). Further, methylene bisthiocyanate, 1,2-bis(bromoacetoxy)ethane, 1,4-bis(bromoacetoxy)-2-butene and the like have microbistatic action, but are required to be maintained in a high concentration for a long period in order to be effective.

Therefore, the above mentioned ingredients are often used in combination and this can sometimes demonstrate a synergistic effect. But the effective combinations are limited in number. In addition, it is also known that when a composition containing a single ingredient is continuously used, resistant bacteria appear which decreases the effect of the composition.

Further, the temperature of industrial process water or industrial products to be subjected to a microbicidal/microbistatic treatment will vary greatly depending on the season or other factors. For example, the temperature of papermaking process water is about 40° C. in summer but drops to 15° C. or lower in winter. Such a temperature drop is known to be a factor markedly reducing the microbicidal/microbistatic effects of bactericidal compositions.

The purpose of the present invention is to provide a composition which can exhibit effective microbicidal/microbistatic action in small amounts and can maintain its effectiveness even at lower temperatures.

Nitrobromopropane derivatives of the formula (I) as given below are known from the disclosures in Japanese Published Examined patent application No. 16460/1968, EPA No. 36055 and EPA No. 34684 to have microbicidal activity but they are not known to exhibit a synergistic effect in combination with other agent(s) and maintain this effect even at low temperatures.

On the other hand, 2,2-dibromo-3-nitrilopropionamide as disclosed in for example Japanese Published Unexamined patent application No. 91108/1986, is known to have a microbicidal effect by itself and also exert a synergistic effect by its combined use with 4,5-dichloro-1,2-dithiol-3-one. However, the combination use of the above compound and the nitrobromopropane derivatives of the formula (I) is not known.

SUMMARY OF THE INVENTION

Thus, according to the present invention, there is provided a microbicidal/microbistatic composition for industrial use comprising as active ingredients a nitrobromopropane derivative of the formula (I):

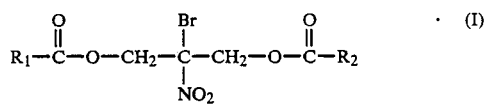

wherein $R_1$ and $R_2$ are the same and are a hydrogen atom or a methyl group, and 2,2-dibromo-3-nitrilopropionamide. Further, there is provided a method of killing or inhibiting the growth of microorganisms by using the above active ingredients in a industrial medium.

DETAILED DESCRIPTION OF THE PREFERRED EMBODIMENT

Figure 1:
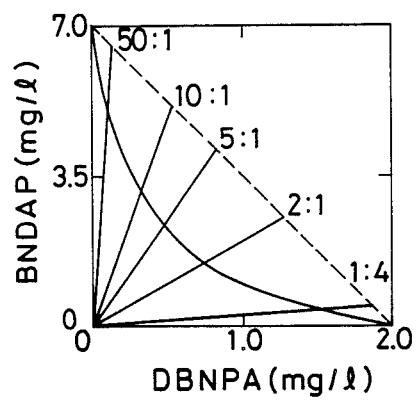
FIGS. 1 to 4 and 6 to 13 are graphs showing the synergistic effects of microbicidal/microbistatic compositions of the present invention.

The compounds of the formula (I) in the present invention include 2-bromo-2-nitro-1,3-diacetyloxypropane(referred to as BNDAP hereafter) and 2-bromo-2-nitro-1,3-diformyloxypropane(referred to as BNDFP hereafter). The ratio of the compound of the formula (I) and 2,2-dibromo-3-nitrilopropionamide(referred to as DBNPA hereafter) is suitably 60:1 to 1:20 (by weight), preferably 50:1 to 1:10, from the viewpoint of microbicidally synergistic effect. On the other hand, from the viewpoint of microbistatically synergistic effect, it is suitably 20:1 to 1:30, and preferably 10:1 to 1:10.

The two kinds of active ingredients in the present invention are usually used in a single-pack preparation to industrial media requiring microbicidal/microbistatic treatment. However they may be added separately (as they are or separate preparations) to the industrial media to be treated. Generally the single-pack preparation is preferable.

In order to prepare the single-pack liquid preparation, organic solvents and dispersing agents are generally used. When the formulation is to be used in an industrial water system, such as in papermaking process water, industrial cooling water and the like, the preparation preferably may be prepared by use of hydrophilic organic solvents and dispersing agents to ensure solubility or dispersibility of the ingredients in water. Examples of such hydrophilic organic solvents are amides, such as dimethylformamide; glycols, such as ethylene glycol, propylene glycol, diethylene glycol and dipropylene glycol; glycol ethers, such as methyl cellosolve, phenylcellosolve, diethylene glycol monomethyl ether, dipropylene glycol monomethyl ether and tripropylene glycol monomethyl ether; alcohols containing up to 8 carbon atoms, such as methanol, ethanol, propanol, butanol and octanol; and esters such as methyl acetate, ethyl acetate, 3-methoxybutyl acetate, 2-ethoxymethyl acetate, 2-ethoxyethyl acetate and propylene carbonate. The hydrophilic organic solvents may be used singly or in mixture thereof and also may contain a small amount of water.

It is preferable from the viewpoint of storage stability to use dimethylformamide or esters such as methyl acetate, ethyl acetate, propyl acetate, 3-methoxybutyl acetate, 2-ethoxymethyl acetate, 2-ethoxy ethyl acetate and propylene carbonate and it is more preferable to use dimethylformamide or propylene carbonate.

Examples of suitable dispersing agents are cationic, anionic, nonionic and amphoteric surfactants, nonionic surfactants being preferred because of stability of their preparations. Specifically, the nonionic surfactants include higher alcohol ethylene oxide (EO) adducts, alkyl-phenol-EO adducts, fatty acid-EO adducts, fatty acid polyhydric alcohol ester-EO adducts, higher alkylamine-EO adducts, fatty acid amide-EO adducts, fat-EO adducts, propylene oxide (PO)-EO copolymers, alkylamine PO-EO copolymer adducts, fatty acid glycerol esters, fatty acid pentaerythritol esters, fatty acid sorbitol esters, fatty acid sorbitan esters, fatty acid sucrose esters, polyhydric alcohol alkyl esters and alkylolamides.

The single-pack liquid preparation preferably comprises 1 to 50 parts by weight of the total separation of the active ingredients and at least 0.01 part by weight of the dispersing agent per part of the active ingredients, the balance being the hydrophilic organic solvent.

The preparation may be added in the form of an single-pack liquid preparation to an oil medium such as heavy oil sludege, cutting oil or oily paint using a hydrophobic organic solvent, e.g., a hydrocarbon solvent such as kerosene, heavy oil or spindle oil, and optionally containing an appropriate surfactant.

To the medium in which the active ingredients of the invention can be directly dissolved or dispersed, the active ingredients may be added directly or in the form of an single-pack powdery preparation which is diluted with solid diluents (e.g., kaolin, clay, bentonite or carboxymethylcellulose) and optionally contains various surfactants. The powdery preparation may be prepared by blending the active ingredients and solid diluent without solvents, depending on the combination of the active ingredients.

A suitable amount of the microbicidal/microbistatic composition of the invention to be added depends on the condition of the industrial medium and the object to be attained. In particular, to papermaking process water or industrial cooling water, the addition of about 0.05 to 200 mg/l as the total active ingredients concentration in the water will be sufficient for inhibiting the growth of microbes(microbistatic effect) and the addition of 0.5 to 50 mg/l will achieve a microbicidal effect.

In the method according to the present invention, the use of the above mentioned single-pack preparation is convenient. However, separate preparations containing each of the active ingredients may be used if desired.

Microbicidal effect

In the combination of BNDAP and DBNPA, or BNDFP and DBNPA as active ingredients, the minimum concentration (mg/l) of the ingredients required to decrease an initial number of $10^6$ or more/ml of viable bacteria, such as Pseudomonus aeruginosa or Staphylococcus aureus, to $10^3$ or less/ml (with microbicidal effect of 99.9% or more) was determined.

The measuring method to determine the minimum concentration is as follows.

A bouillon broth was inoculated with the bacteria and preincubated. The obtained culture was added to a physiological saline so that the number of viable bacteria in the mixture becomes $10^6$ or more/ml. The above ingredients were added to the resultant culture and shaken for 1 hour at 37° C. The number of surviving bacteria was measured, to determine the minimum concentration required.

Figure 2:
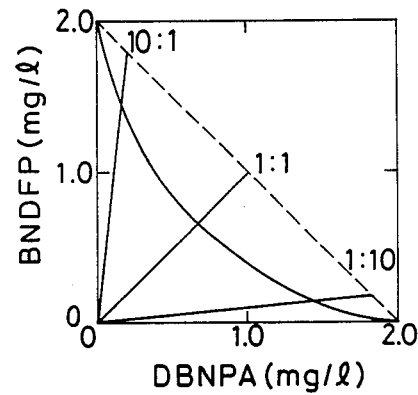
Figure 3:
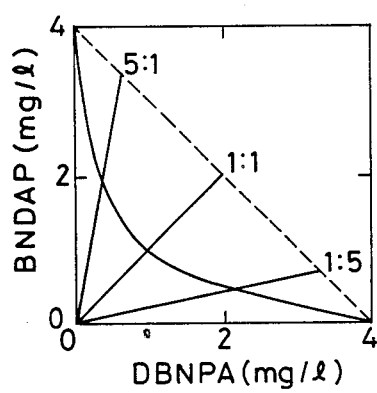
Figure 4:
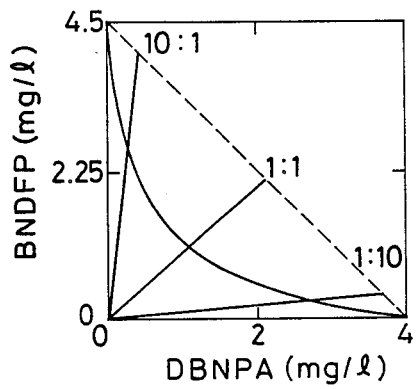

The results on Pseudomonas aeruginosa are shown in FIGS. 1 and 2, and those on Staphylococcus aureus are shown in FIGS. 3 and 4.

Microbistatic effect (1) Evaluation method

A synergistic effect of the combination of the two kinds of ingredients was examined in accordance with the two-dimensional dilution method. Each of the two ingredients was diluted to a predetermined concentration, and a predetermined amount of the resultant solution was added to a bouillon broth. The broth was inoculated with a microorganism and incubated under constant condition. The concentration of the ingredients at which no growth of the microorganism was observed was defined as the minimum inhibitory concentration according to the two-dimensional dilution method (hereinafter abbreviated to TDMIC).

Figure 5:
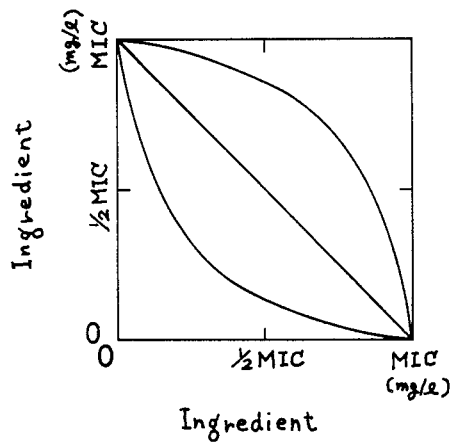
FIG. 5 is a graph explaining a criterion of synergistic effect

FIG. 5 is a sample of the graph wherein the minimum inhibitory concentrations (MIC. mg/l) of the respective ingredients used alone are expressed by an equal length on the vertical and horizontal axes. In this Figure, the area above the curve, i.e., the TDMIC curve shows the growth inhibition area and the area below the curve is the growth area. A curve positioned over the diagonal line means an antagonistic effect and a curve positioned below the diagonal line expresses a synergistic effect.

(2) Synergistic effect against bacteria

The synergistic effect of BNDAP and DCDP, or BNDFP and DCDP was examined against Pseudomonas aeruginosa, a typical Gram-negative bacteria which was separated from a slime. The bacteria was preincubated overnight. A bouillon broth was inoculated with a predetermined amount of the resultant culture, and shaken for 24 hours at 37° C. The concentration of the ingredients at which no turbidity of the broth was observed was determined.

Figure 6:
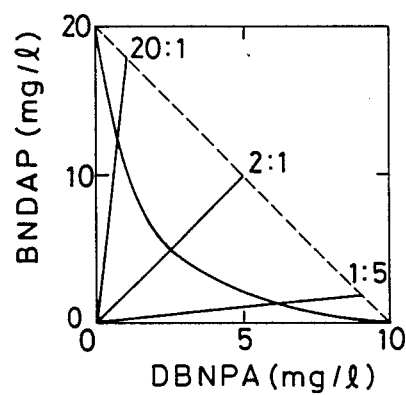
Figure 7:
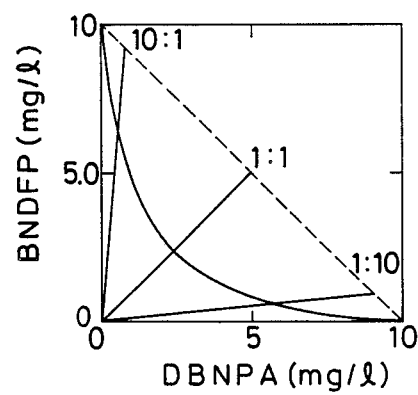

The results are shown in FIGS. 6 and 7.

(3) Synergistic effect against fungi

Figure 8:
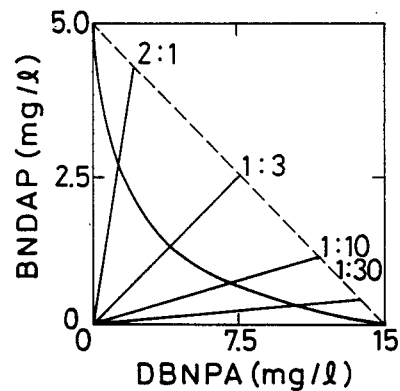
Figure 9:
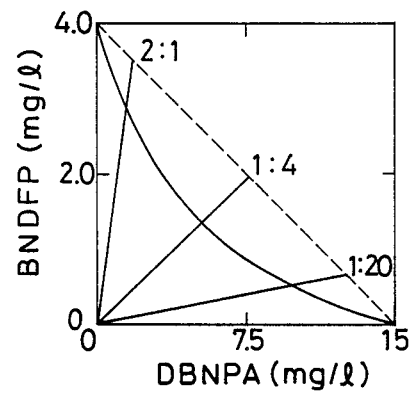
Figure 10:
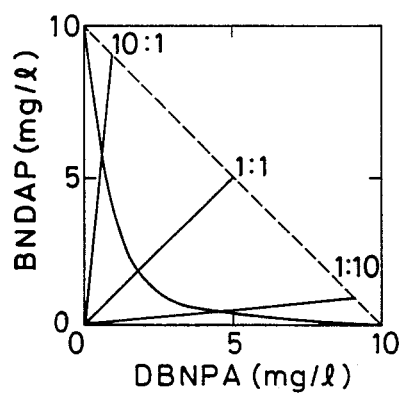
Figure 11:
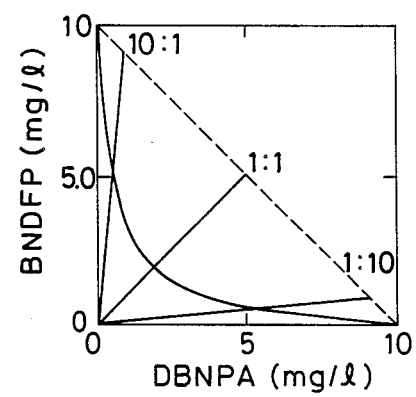

The synergistic effect of the ingredients was examined against Aspergillus niger and Gliocladium virens which are fungi and often occur in wet pulp, starch glue, and coating color. From the strain which was beforehand slant-cultured using Czapek medium, one loopful of the spores was taken and suspended in sterilized water. A Czapek broth was inoculated with a predetermined amount of the suspension and shaken for 7 days at 27° C. The concentration of the ingredient at which no growth of the mycelia was observed was determined. The results on Aspergillus niger are shown in FIGS. 8 and 9, and the results on Gliocladium virens are shown in FIGS. 10 and 11.

(4) Synergistic effect against yeast

The synergistic effect against a typical yeast, Rhodotorula rubula which is often found in starch liquid and coating color liquid was examined.

Figure 12:
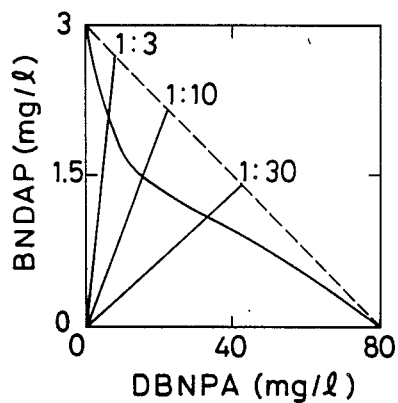
Figure 13:
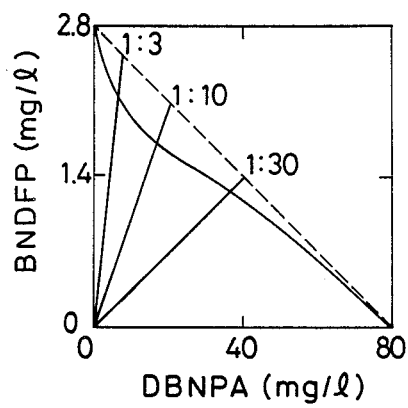

Using YM broth, the yeast was preincubated overnight. With a predetermined amount of the obtained culture solution, a YM broth was inoculated and incubated with shaking for 24 hours at 30° C. The concentration of the ingredient at which no turbidity of the broth was observed was determined. The results are shown in FIGS. 12 and 13.

Microbicidal effect in white water of papermaking process

In a certain paper mill, white water was sampled from a papermaking machine for fine paper (neutral paper). The white water had a pH of 7.4 and contained 8 ppm of $SO_3^{2-}$ and viable microbes mainly consisting of Flavobacterium, Micrococcus, Pseudomonas and Bacillus species. The above ingredients were added to the white water. The resulting white water was shaken for 60 minutes at 37° C. and the number of viable bacteria was determined. The results are shown in Table 1.

TABLE 1

| Ingredient | Concentraton of ingredient (mg/l) | Number of viable bacteria per ml |
|---|---|---|
| Not added Comparative Example | 0 | $1.5 \times 10^7$ |
| BNDAP | 7.5 | $5.6 \times 10^6$ |
|  | 15 | $9.2 \times 10^5$ |
| DBNPA | 7.5 | $7.2 \times 10^6$ |
|  | 15 | $1.3 \times 10^6$ |
| Example |  |  |
| BNDAP + DBNPA (1:1) | 7.5 | $3.6 \times 10^4$ |
|  | 15 | $1.9 \times 10^3$ |
| BNDAP + DBNPA (1:2) | 7.5 | $2.3 \times 10^4$ |
|  | 15 | $1.3 \times 10^3$ |
| BNDFP + DBNPA (1:1) | 7.5 | $1.4 \times 10^4$ |
|  | 15 | $2.0 \times 10^3$ |
| BNDFP + DBNPA (1:2) | 7.5 | $2.5 \times 10^4$ |
|  | 15 | $3.1 \times 10^3$ |
| Comp. Ex. |  |  |
| DBNPA + DBNE*1 (1:1) | 7.5 | $9.8 \times 10^6$ |
|  | 15 | $5.6 \times 10^6$ |
| DBNPA + DCDT*2 | 7.5 | $7.5 \times 10^6$ |

TABLE 1-continued

| Ingredient | Concentraton of ingredient (mg/l) | Number of viable bacteria per ml |
|---|---|---|
| (1:1) | 15 | $3.3 \times 10^6$ |

*1DBNE means 2,2-dibromo-2-nitro-1-ethanol.
*2DCDT means 4,5-dichloro-1,2-dithiol-3-one.

Consideration

As seen clearly from the results, any of the single ingredients and the combination of DBNE+DCDT only slightly decreased the number of viable bacteria and therefore they are not considered to have a microbicidal effects. However, the combinations of BNDAP+DBNPA, and BNDFP+DBNPA show very great synergistic effects in their microbicidal power.

Influence of temperature on microbicidal effect in white water of papermaking process In a paper mill, white water was sampled from a papermaking machine for fine paper (neutral paper). The white water had a pH of 7.0 and contained 0 ppm of $SO_3^{2-}$ and viable microbes mainly consisting of Pseudomonas, Bacillus, Alcaligenes and Klebsiella species. The above ingredients were added to the white water. The resulting white water was shaken for 60 minutes at 15° C. or 35° C. and the number of viable bacteria was determined. The results are shown in Table 2.

TABLE 2

| Ingredient | Concentration of ingredient (mg/l) | Number of viable bacteria per ml 35° C. | 15° C. |
|---|---|---|---|
| Not added Comparative Example | 0 | $3.5 \times 10^7$ | $2.7 \times 10^7$ |
| BNDAP | 10 | $9.8 \times 10^6$ | $1.5 \times 10^7$ |
|  | 20 | $6.8 \times 10^6$ | $8.3 \times 10^6$ |
| BNDFP | 10 | $7.9 \times 10^6$ | $8.7 \times 10^6$ |
|  | 20 | $5.1 \times 10^6$ | $6.5 \times 10^6$ |
| DBNPA | 10 | $5.9 \times 10^6$ | $8.3 \times 10^6$ |
|  | 20 | $4.1 \times 10^6$ | $7.8 \times 10^6$ |
| Example |  |  |  |
| BNDAP + DBNPA (1:1) | 10 | $3.4 \times 10^4$ | $6.8 \times 10^4$ |
|  | 20 | $1.1 \times 10^3$ | $3.0 \times 10^3$ |
| BNDAP + DBNPA (1:10) | 10 | $7.1 \times 10^3$ | $8.9 \times 10^3$ |
|  | 20 | $10^3$ less | $1.5 \times 10^3$ |
| BNDAP × DBNPA (10:1) | 10 | $2.5 \times 10^4$ | $3.1 \times 10^4$ |
|  | 20 | $1.3 \times 10^3$ | $2.5 \times 10^3$ |
| BNDFP + DBNPA (1:1) | 10 | $3.0 \times 10^4$ | $3.5 \times 10^4$ |
|  | 20 | $2.1 \times 10^3$ | $2.9 \times 10^3$ |
| BNDFP + DBNPA (1:10) | 10 | $9.9 \times 10^3$ | $1.5 \times 10^4$ |
|  | 20 | $1.0 \times 10^3$ | $2.3 \times 10^3$ |
| BNDFP + DBNPA (10:1) | 10 | $9.5 \times 10^3$ | $9.9 \times 10^3$ |
|  | 20 | $1.5 \times 10^3$ | $2.7 \times 10^3$ |
| Comparative Example |  |  |  |
| DCDT$^1$ + DBNPA (1:5) | 10 | $3.0 \times 10^6$ | $7.5 \times 10^6$ |
|  | 20 | $2.2 \times 10^6$ | $6.1 \times 10^6$ |
| DBNE$^2$ + DBNPA (1:1) | 10 | $8.8 \times 10^6$ | $1.1 \times 10^7$ |
|  | 20 | $7.7 \times 10^6$ | $9.5 \times 10^6$ |
| DBNE + DCDT (5:1) | 10 | $1.3 \times 10^6$ | $9.0 \times 10^6$ |
|  | 20 | $5.1 \times 10^5$ | $7.9 \times 10^6$ |
| BBAE$^3$ + DCDT (5:1) | 10 | $3.0 \times 10^5$ | $9.1 \times 10^6$ |
|  | 20 | $9.8 \times 10^4$ | $8.1 \times 10^6$ |
| MBTC$^4$ × DBNPA (1:2) | 10 | $8.9 \times 10^4$ | $7.9 \times 10^6$ |
|  | 20 | $2.1 \times 10^4$ | $5.3 \times 10^6$ |
| DCDT + BTBMS$^5$ (1:2) | 10 | $9.7 \times 10^4$ | $3.3 \times 10^6$ |
|  | 20 | $1.9 \times 10^4$ | $9.1 \times 10^5$ |
| MIT$^6$ + BBAB$^7$ | 10 | $7.7 \times 10^5$ | $8.7 \times 10^6$ |

TABLE 2-continued

| Ingredient | Concentration of ingredient (mg/l) | Number of viable bacteria per ml 35° C. | Number of viable bacteria per ml 15° C. |
|---|---|---|---|
| (1:3) | 20 | $6.9 \times 10^4$ | $5.5 \times 10^6$ |

[1] DCDT: 4,5-Dichloro-1,2-dithiol-3-one
[2] DBNE: 2,2-Dibromo-2-nitro-1-ethanol
[3] BBAE: Bisbromoacetoxyethane
[4] MBTC: Methylene bisthiocyanate
[5] BTBMS: Bistribromomethylsulfone
[6] MIT: 5-Chloro-2-methyl-4-isothiazoline-3-one
[7] BBAB: Bisbromoacetoxy-2-butene

Consideration

As seen from the results, the ingredients singly or the combination of DCDT+DBNPA or DBNE+DBNPA only slightly decreases the number of viable bacteria and therefore they are not considered to have a microbicidal effect which can prevent the growth of microorganisms.

The combinations of BBAE+DCDT, MBTC+DBNPA, DCDT +BTBMS and MIT+BBAB each exhibited a synergistic effect in their microbicidal effect at 35° C. But when the temperature dropped into 15° C., their microbicidal effect greatly decreased and the synergistic effects shown at 35° C. disappeared.

On the other hand, the combinations of BNDAP+DBNPA and BNDFP+DBNPA were observed to have very great synergistic effect. Further, the effect was maintained even if the temperature dropped from 35° C. to 15° C. Thus the above combinations are considered to be very useful as microbicidal agents.

Storage stability of the ingredients in single-pack liquid preparation

Single-pack liquid preparations were prepared by dissolving BNDAP+DBNPA or BNDFP+DBNPA in various organic solvents, with percentage by weight described in Table 3.

After they were allowed to stand stood for leave in a thermostatic chamber for 30 days at 50° C., the residual amount of each the ingredients was determined with high-pressure liquid chromatography(HPLC) and then the percentage of their residual quantity was calculated. The results are shown in Table 3.

TABLE 3

| Solvent | (Residual quantity %) Active ingredient (% by weight) BNDAP 10 (w/w %) | DBNPA 2 (w/w %) | BNDFP 10 (w/w %) | DBNPA 2 (w/w %) |
|---|---|---|---|---|
| PC | 99 | 99 | 100 | 99 |
| MBA | 98 | 81 | 96 | 80 |
| MDG | 61 | 90 | 50 | 89 |
| DMF | 97 | 89 | 95 | 85 |
| DEG | 49 | 92 | 33 | 90 |

PC: Propylene carbonate
MBA: 3-Methoxybutyl acetate
MDG: Diethylformide
DMF: Dimethylformide
DEG: Diethylene glycol

EXAMPLE

In a certain paper mill, the number of viable bacteria in white water in a linerboard machine (production 200 tons/day) was $10^7$/ml and a large quantity of slime was found resulting in pinholes being formed on the paper products.

An single-pack liquid preparation of 10 wt% of BNDAP, 10 wt% of DBNPA and 80 wt% of propylene carbonate was added to the stuff box part for each ply three times a day, each time for 1 hour, at a level of 47 ppm based on the pulp slurry. As a result, the number of viable bacteria decreased to $10^3$/ml and the quantity of slime greatly decreased the pinhole trouble was then resolved.

The microbicidal/microbistatic compositions for industrial use and the industrial microbicidal/microbistatic method of the present invention exhibit excellent microbicidal/microbistatic effects and can accomplish intended microbicidal/microbistatic treatments with a lower concentration of ingredients. Further, the microbicidal/microbistatic compositions of the present invention are also very useful because their microbicidal and microbistatic power are not affected by temperature fluctuation, particularly decreasing temperatures.

We claim:

1. A microbicidal/microbistatic composition for industrial use comprising, as active ingredients, a nitrobromopropane derivative of the formula (I):

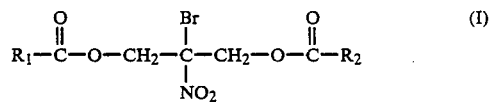

wherein $R_1$ and $R_2$ are the same and are a hydrogen atom or a methyl group, and 2,2-dibromo-3-nitrilopropionamide in a ratio of from 10:1 to 1:10 by weight.

2. The composition of claim 1 which is in the form of a single-pack liquid preparation together with an organic solvent and a dispersing agent.

3. The composition of claim 2 in which the organic solvent is a hydrophilic organic solvent selected from amides, glycols and, glycol ethers, alcohols and esters.

4. The composition of claim 3 in which the hydrophilic organic solvent is dimethylformamide, methyl acetate, ethyl acetate, propyl acetate, 3-methoxybutyl acetate, 2-ethoxymethyl acetate, 2-ethoxyethyl acetate or propylene carbonate.

5. The composition of claim 2 in which the organic solvent is a hydrophobic organic solvent such as kerosene, heavy oil or spindle oil.

6. The composition of claim 2 in which the dispersing agent is a nonionic surfactant.

7. The composition of claim 1 which is in the form of an single-pack powdery preparation together with a solid diluent.

8. The composition of claim 7 in which the solid diluent is kaolin, clay, bentonite or carboxymethylcellulose.

9. A method of killing or inhibiting the growth of microorganisms which comprises adding to an industrial medium a nitrobromopropane derivative of the formula (I):

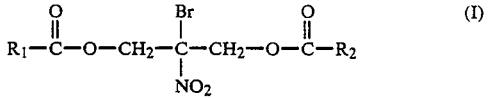

wherein $R_1$ and $R_2$ are the same and are a hydrogen atom or a methyl group, and 2,2-dibromo-3-nitrilopropionamide, serpately or simultaneously in a ratio by weight of from 10:1 to 1:10.

10. The method of claim 9 in which the total amount of the compound of the formula (I) and 2,2-dibromo-3-nitrilopropionamide added to the industrial medium is 0.05 to 200 mg/l.

11. The method of claim 9 in which the industrial medium is papermaking process water, cooling water and washing water for various industry, heavy oil sludges, cutting oils, textile oils, paints, antifouling coatings, paper coating liquids, latices or sizings.

* * * * *